(12) United States Patent
Girard et al.

(10) Patent No.: US 8,575,211 B2
(45) Date of Patent: Nov. 5, 2013

(54) SYNERGISTIC COMBINATION OF ANALGESIC COMPOUNDS

(75) Inventors: Philippe Girard, Margny-les-Compiegne (FR); Marie-Emmanuelle Le Guern, Compiegne (FR); Laurence Berthon-Cedille, Ricquebourg (FR); Jean-Marie Gillardin, Jonquieres (FR); Bernard Hublot, Compiegne (FR)

(73) Assignee: Biocodex, Gentilly (FR)

( * ) Notice: Subject to any disclaimer, the term of this patent is extended or adjusted under 35 U.S.C. 154(b) by 549 days.

(21) Appl. No.: 12/607,213

(22) Filed: Oct. 28, 2009

(65) Prior Publication Data

US 2010/0197777 A1      Aug. 5, 2010

(30) Foreign Application Priority Data

Oct. 29, 2008 (FR) ...................................... 08 57363

(51) Int. Cl.
| | |
|---|---|
| *A61K 31/55* | (2006.01) |
| *A61K 31/192* | (2006.01) |
| *A61K 31/395* | (2006.01) |
| *A61P 25/04* | (2006.01) |

(52) U.S. Cl.
USPC ............................ 514/450; 514/506; 514/532

(58) Field of Classification Search
USPC .......................................... 514/450, 506, 532
See application file for complete search history.

(56) References Cited

U.S. PATENT DOCUMENTS

2002/0028238 A1 *   3/2002   Karim et al. .................. 424/461

OTHER PUBLICATIONS

Moffat, "Postoperative nefopam and diclofenac. Evaluation of their morphine-sparing effect after upper abdominal surgery", Anaesthesia, Apr. 1990, 45(4), pp. 302-305.*

* cited by examiner

*Primary Examiner* — Renee Claytor
*Assistant Examiner* — Sahar Javanmard
(74) *Attorney, Agent, or Firm* — B. Aaron Schulman; Stites & Harbison, PLLC

(57) ABSTRACT

The present invention relates to a pharmaceutical composition comprising as active substances:
  at least one compound of the following general formula (I):

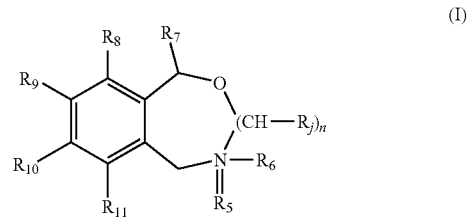

and
  at least one compound of the following general formula (V):

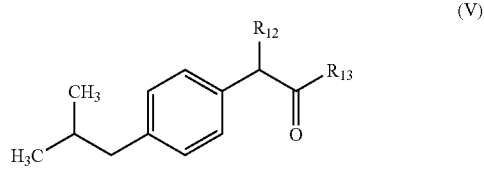

especially for its use in the prevention or treatment of pain.

10 Claims, 1 Drawing Sheet

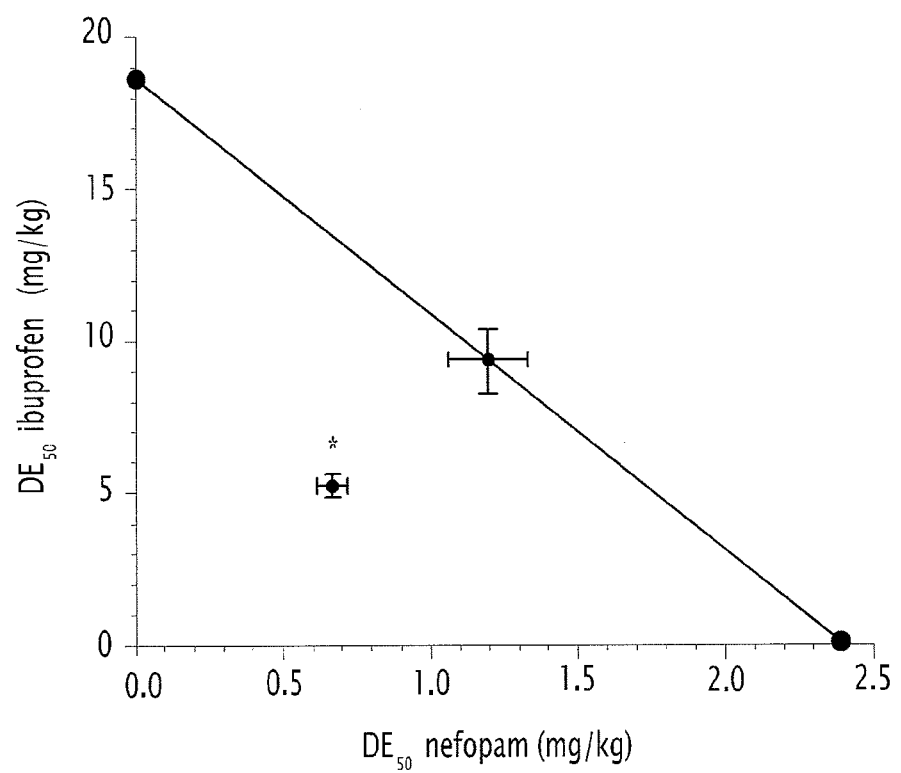

SYNERGISTIC COMBINATION OF ANALGESIC COMPOUNDS

FIELD OF THE INVENTION

The present invention relates to a pharmaceutical composition comprising compounds having a synergistic action in the prevention or treatment of pain.

TECHNICAL BACKGROUND

Nefopam is the active ingredient of Acupan®. It is a non-opioid centrally acting antalgic of the benzoxazocine family (Klohs et al. (1972) *Arzneimittelforschung* 22:132-3). Its advantages include, in particular, the absence of respiratory depressant effects. Its mode of action is still not properly understood but seems to require monoamine uptake inhibition, which distinguishes it from paracetamol and non-steroidal anti-inflammatories (NSAIDs). NSAIDs are more or less selective inhibitors of the cyclooxygenase isoform 2 (COX-2) which thus have the effect of reducing the synthesis of prostaglandins in the central and peripheral nervous systems.

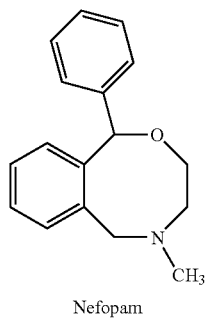 [SMILES: CN1CCOC(c2ccccc2)c2ccccc2C1]

Nefopam

Currently, nefopam is principally used for the treatment of post-operative pain. In France, it is thus administered to approximately 20% of patients who have undergone surgical intervention (Fletcher et al. (2008) *Pain* 137:441-51). However, its own analgesic efficacy is sometimes not sufficient in painful surgeries and it is in fact often used in combination with other analgesics, in particular morphine, paracetamol and ketoprofen (NSAID) (Fletcher et al. (2008) *Pain* 137: 441-51). However, those combinations have certain limitations.

Thus, although it permits a notable reduction in the amount of morphine administered for the same analgesic efficacy, the nefopam-morphine combination does not always enable the doses of morphine to be reduced sufficiently to eliminate the undesirable symptoms associated with its use (Du Manoir et al. (2003) *Br. J. Anaesth.* 91:836-841). The effect of the nefopam-ketoprofen combination has for its part been evaluated post-operatively as being synergistic, but only after moderately painful surgeries (Delage et al. (2005) *Anesthesiology* 102:12111216). In addition, the use of ketoprofen is often limited in time owing to its poor digestive tolerance.

It therefore remains to find a combination which makes it possible to benefit from the advantages of nefopam while at the same time offering some comfort of use for the patient.

Therefore, the analgesic efficacy of a combination of nefopam and diclofenac, another NSAID, has also been evaluated without any benefit being demonstrated compared with the use of diclofenac alone (Moffat et al. (1990) *Anesthesia* 45:302-305).

Ibuprofen is also a NSAID which brings about analgesia which is efficacious but less so than that of ketoprofen (Mills et al. (1973) *British Medical Journal* 4:82-84). Currently, ibuprofen is hardly ever used in the management of post-operative pain (Fletcher et al. (2008) *Pain* 137:441-51).

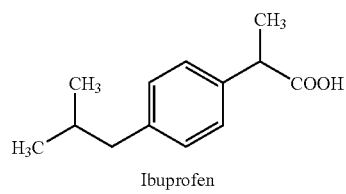

Ibuprofen

SUMMARY OF THE INVENTION

The present invention follows from the unexpected discovery, by the inventors, of a synergistic analgesic effect between nefopam and ibuprofen in an animal model of acute pain.

Thus, the present invention relates to a pharmaceutical composition comprising as active substances:

a) at least one compound of the following general formula (I):

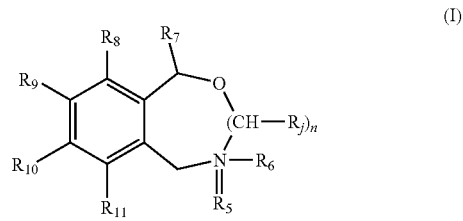

(I)

wherein:

$R_5$ represents O or no group;

$R_6$ represents H or an alkyl group containing from 1 to 6 carbon atoms;

n represents an integer from 2 to 4;

j represents an integer ranging from 1 to n;

$R_j$, which is identical or different for each substituted carbon, represents H or an alkyl group containing from 1 to 6 carbon atoms;

$R_7$ represents a phenyl group optionally substituted by one or more identical or different groups selected from the list comprising H, an alkyl group containing from 1 to 6 carbon atoms, an alkoxy group containing from 1 to 6 carbon atoms, a trifluoromethyl group, or a halogen atom;

$R_8, R_9, R_{10}, R_{11}$, which are identical or different, represent H, an alkyl group containing from 1 to 6 carbon atoms, an alkoxy group containing from 1 to 6 carbon atoms, a trifluoromethyl group, or a halogen atom;

or a pharmaceutically acceptable salt of that compound; and b) at least one compound of the following general formula (V):

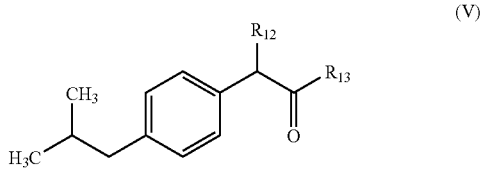

(V)

wherein:

$R_{12}$ represents H or an alkyl group containing from 1 to 6 carbon atoms;

$R_{13}$ represents a group $OR_{14}$ or $NR_{15}R_{16}$;

$R_{14}$ represents H, an alkyl group containing from 1 to 6 carbon atoms, an aryl group containing from 6 to 10 carbon atoms, or an aralkyl or alkaryl group containing from 7 to 20 carbon atoms;

$R_{15}$ and $R_{16}$, which are identical or different, represent H, OH, an alkyl group containing from 1 to 6 carbon atoms, an aryl group containing from 6 to 10 carbon atoms, or an aralkyl or alkaryl group containing from 7 to 20 carbon atoms;

or a pharmaceutically acceptable salt of that compound;

which are optionally combined with one or more pharmaceutically acceptable excipients, in particular for inducing analgesia or for its use in the prevention or treatment of pain.

The present invention relates also to a compound of the general formula (I) as defined above, or a pharmaceutically acceptable salt thereof, in combination with a compound of the general formula (V) as defined above, or a pharmaceutically acceptable salt thereof, for their use as a medicament, in particular for inducing analgesia or preventing or treating pain.

The present invention relates also to the use of a compound of the general formula (I) as defined above, or of a pharmaceutically acceptable salt thereof, in combination with a compound of the general formula (V) as defined above, or a pharmaceutically acceptable salt thereof, in the preparation of a medicament which is analgesic or which is for the prevention or treatment of pain.

The present invention relates also to a method for inducing analgesia or for preventing or treating pain in an individual, in which method the individual is administered a prophylactically or therapeutically effective amount of at least one compound of the general formula (I) as defined above, or of a pharmaceutically acceptable salt thereof, and a prophylactically or therapeutically effective amount of at least one compound of the general formula (V) as defined above, or of a pharmaceutically acceptable salt thereof.

The present invention relates also to products containing:

at least one compound of the general formula (I) as defined above, or a pharmaceutically acceptable salt thereof, and at least one compound of the general formula (V) as defined above, or a pharmaceutically acceptable salt thereof, as a combination product to be used together or separately in order to induce analgesia or in order to prevent or treat pain.

In a preferred embodiment of the pharmaceutical composition, the compounds, the use, the method and the products defined above, at least one additional analgesic or antalgic compound which is different from the compounds of the general formulae (I) and (V) as defined above, or from their pharmaceutically acceptable salts, is added in combination with the compounds of the general formulae (I) and (V) as defined above.

DESCRIPTION OF FIG. 1

FIG. 1 represents the isobologram of the ibuprofen-nefopam combination in the acetic acid-induced cramp test in mice. The star symbol (*) indicates that the point representing the ED50 of the ibuprofen-nefopam combination measured experimentally is located beneath the line of additivity in a statistically significant manner.

DETAILED DESCRIPTION OF THE INVENTION

Prevention or Treatment of Pain

The expression "to treat pain" means to reduce or eliminate pain or sensitivity to that pain. The expression "to prevent pain" means that the compounds of the general formulae (I) and (V) as defined above, or pharmaceutically acceptable salts thereof, are administered to an individual before that individual perceives the pain to be treated.

The expression "to induce analgesia" means to reduce or eliminate both pain and sensitivity to that pain. It is here considered that this expression is equivalent to "use as an analgesic or antalgic".

Preferably, the pain prevented or treated according to the invention is acute pain. The expression "acute pain" is well known to the person skilled in the art. It is the opposite of the notion of "chronic pain". It is generally considered that acute pain is pain whose duration is less than three months.

Preferably also, the pain prevented or treated according to the invention is acute post-operative pain. "Acute post-operative pain" denotes pain caused by surgical intervention, in particular surgical intervention involving an incision, the cicatrization of which creates pain of the inflammatory type with hyperalgesic participation, for an average period of 5 to 7 days (Chauvin and Clergue (1998) *Ann. Fr. Anesth. Réanim.* 17:444).

Preferably, the intensity of the pain prevented or treated according to the invention is at least moderate, more preferably at least severe (also referred to as intense). The notions of "moderate pain" or "severe pain" are well known to the person skilled in the art. By way of example, it is generally considered that moderate pain corresponds to an index of 4 to 6 and severe pain to an index of 7 to 9 on a numerical scale of pain graded from 0 to 10. On that same scale, the index 0 corresponds to an absence of pain, the index 1 to 3 to slight pain, and the index 10 to the maximum pain imaginable.

Compound of the General Formula (I)

Preferably, the compound of the general formula (I) defined above is represented by one of the following formulae (II), (III) and (IV):

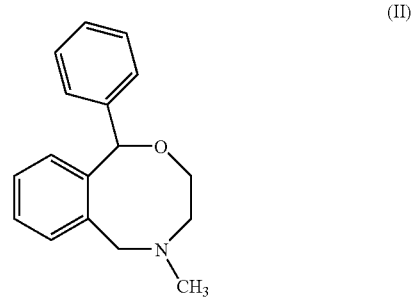

(II)

-continued

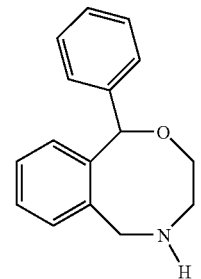
(III)

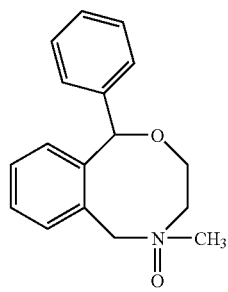
(IV)

Formula (II) represents nefopam, and formulae (III) and (IV) represent, respectively, two metabolites of nefopam, namely desmethyl nefopam and nefopam N-oxide.

In a particularly preferred manner, the compound of the general formula (I) as defined above is represented by the above formula (II).

As understood here, the general formula (I) defined above also represents the stereoisomers and mixtures of stereoisomers, especially the racemic mixture, of the compounds of formula (I).

The pharmaceutically acceptable salts of the compounds of the general formula (I) defined above will be clearly apparent to the person skilled in the art. In particular, the hydrochloride salts of the compounds of the general formula (I) as defined above are preferred.

Nefopam hydrochloride is the compound of the general formula (I) as defined above which is the most preferred for the implementation of the invention.

Compound of the General Formula (V)

The compound of the general formula (V) defined above is preferably represented by the following formula (VI):

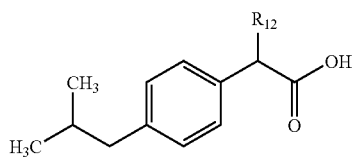
(VI)

wherein $R_{12}$ is as defined above.

Likewise preferably, the compound of the general formula (V) defined above is represented by the following formulae (VII), (VIII) and (IX):

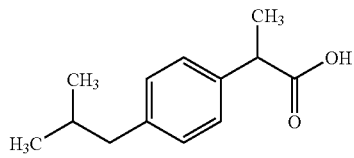
(VII)

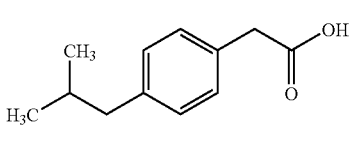
(VIII)

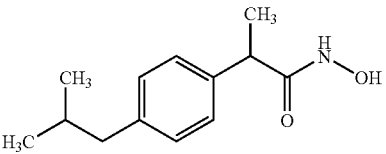
(IX)

The above formulae (VII), (VIII) and (IX) represent ibuprofen, ibufenac and ibuproxam, respectively.

In a more preferred manner, the compound of the general formula (V) defined above is represented by the above formula (VII) and in a particularly preferred manner by the following formula (X):

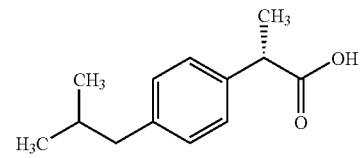
(X)

Formula (X) represents the S form of ibuprofen which carries most of the analgesic properties of ibuprofen.

As understood here, the formulae (V), (VI), (VII) and (IX) defined above also represent the stereoisomers and mixtures of stereoisomers, in particular the racemic mixture, of the compounds of formulae (V), (VI), (VII) and (IX).

The pharmaceutically acceptable salts of the compounds of the general formula (V) defined above will be clearly apparent to the person skilled in the art. In particular, the lysine salts, especially the L-lysine salts, of the compounds of the general formula (V) as defined above are preferred, such as the lysine salt of ibuprofen or the monohydrated L-lysine salt of the S form of ibuprofen.

Furthermore, as will be clearly apparent to the person skilled in the art, it is easy to synthesize prodrugs of the compounds of the formulae (VI), (VII) and (VIII) defined above, that is to say, compounds which are rapidly converted in vivo to give the compounds of the formulae (VI), (VII) and (VIII) defined above, for example by hydrolysis in the blood. Therefore, apart from the prodrugs of the compounds of formulae (VI), (VII) and (VIII) defined above which are represented by the compounds of formula (V) for which $R_{13}$ is other than OH, such as ibuproxam, the aim here is to protect the use according to the invention of all of the prodrugs of the compounds of formula (VI) defined above.

Administration

As understood here, the expression "in combination" or "combination product" means that the compound of the general formula (I) as defined above, or a pharmaceutically acceptable salt thereof, and the compound of the general formula (V) as defined above, or a pharmaceutically acceptable salt thereof, can be combined within the same pharmaceutical composition, and therefore administered together, or can be administered separately, that is to say, by distinct administration routes and/or distinct administration regimes, provided that, when they are administered separately, the respective periods of analgesic activity of each of the two compounds overlap completely or partially, in particular in such a manner that the compounds are able to co-operate to exert a synergistic analgesic effect.

Thus, when the compounds are administered separately, the compound of the general formula (I) as defined above, or its pharmaceutically acceptable salt, will preferably be administered within 24 hours of the administration of the compound of the general formula (V) as defined above, or its pharmaceutically acceptable salt, and its administration will optionally be continued on the following days. Conversely, the compound of the general formula (V) as defined above, or its pharmaceutically acceptable salt, will preferably be administered within 24 hours of the administration of the compound of the general formula (I) as defined above, or its pharmaceutically acceptable salt, and its administration will optionally be continued on the following days.

Preferably, the compound of the general formula (I) as defined above, or its pharmaceutically acceptable salt, is administered or is in a form suitable for administration by the oral, intravenous or intramuscular route.

Preferably, the compound of the general formula (V) as defined above, or its pharmaceutically acceptable salt, is administered or is in a form suitable for administration by the oral, injectable or local route.

Preferably, when the compound of the general formula (I) as defined above, or its pharmaceutically acceptable salt, and the compound of the general formula (V) as defined above, or its pharmaceutically acceptable salt, are combined within the same pharmaceutical composition, the latter is administered or is in a form suitable for administration by the oral, injectable or local route.

Preferably, the compound of formula (I) as defined above, or its pharmaceutically acceptable salt, especially nefopam hydrochloride, is contained in the pharmaceutical compositions or the products defined above, or is administered, at a unit dose of from 1 to 120 mg, more preferably at a unit dose of 20 mg.

Preferably, the compound of formula (V) as defined above, or its pharmaceutically acceptable salt, especially ibuprofen, in particular in its S form, is contained in the pharmaceutical compositions or the products defined above, or is administered, at a unit dose of from 1 to 2400 mg, more preferably at a unit dose of 400 mg.

Additional Analgesic or Antalgic Compound

Any analgesic or antalgic compound may be suitable as an additional analgesic or antalgic compound according to the invention; however, it is preferably:
 a morphinic, such as morphine, fentanyl, remifentanil, alfentanil, sufentanil, nalbuphine, pentazocine, codeine, hydrocodeine, dextropropoxyphene, tramadol, buprenorphine, hydromorphone, oxycodone, or pethidine;
 a non-steroidal anti-inflammatory (NSAID), such as ketoprofen, acetylsalicylic acid, mefenamic acid, fenoprofen, aceclofenac, tiaprofenic acid, alminoprofen, diclofenac, etodolac, flurbiprofen, nabumetone, naproxen, meloxicam, piroxicam, tenoxicam, indomethacin sulindac, celecoxib, parecoxib, floctafenine, phenylbutazone, or nimesulide (non-exhaustive list);
 paracetamol, ziconitide, or caffeine.

Example

The analgesic effect of a nefopam-ibuprofen combination was studied in the model of abdominal cramps induced in mice by the intraperitoneal administration of acetic acid. This model of pain induced by a chemical substance corresponds to acute, visceral, inflammatory pain.

A. Equipment and Methods

1. Animals

Male CD1 mice (C. River breed) weighing from 25 to 30 grams are used after an acclimatization of at least 7 days in the animal facility (t°=22±2; hygrometry=50±20%; food SAFE "A04"; nycthemeral cycle: 12 h/12 h (light: 7 h/19 h—darkness: 19 h/7 h)).

2. Protocol

On the day of the experiment, the non-fasting mice are weighed, marked and divided at random into groups of 10. The acetic acid solution (Sigma) is prepared at 0.6% (0.1 ml/10 g) i.e. 60 mg of acetic acid in 10 ml of NaCl at 0.9%.

At t=0, the mouse receives the product under study or the carrier liquid by the subcutaneous route (0.1 ml/10 g). At t=30 minutes, the acetic acid is injected by the intraperitoneal route (0.1 ml/10 g).

A count is taken of the number of abdominal cramps from 5 to 20 minutes after the injection of acetic acid. Clear abdominal cramps characterized by stretching of the hind paws and/or hollowing of the flanks with writhing are regarded as positive.

3. Products

Nefopam hydrochloride (Biocodex, lot 38) (referred to hereinafter simply as nefopam) is dissolved in distilled water or in NaCl at 0.9%. The ibuprofen (Sigma, ref 1-4883) is suspended in Tween 80 at 1%.

4. Statistical Analysis

The test used is a variance analysis based on 3 groups and a Student's t test for 2 groups. The treated group(s) that differ(s) from the control group is (are) then determined.

The effective doses for 50% antinociceptive effect (ED50) are calculated using the PharmToolsPro program (version 1.1.27, McCary Group Inc.) in accordance with the Tallarida (2000) method *Drugs synergism and dose-effect data analysis* CRC Press). At least 10 mice are used for each dose, and at least 3 doses are used to determine the dose-response curve. The dose that produces 50% antinociceptive effect (50% reduction in the number of cramps) is calculated by a standard linear regression analysis of the dose-response curve.

The interaction is evaluated by an isobolographic analysis of the co-administration of a combination of doses at a fixed ratio according to Tallarida (2000) op. cit., Tallarida et al. (1989) *Life Sci.* 45:947-961 and Tallarida et al. (1997) *Life Sci.* 61:PL417-PL425. The isobologram is constructed by joining the ED50 of the ibuprofen with that of the nefopam in order to obtain the additivity line. The ED50 of the combination is determined by linear regression analysis of the dose-response curve and it is compared by at test with a theoretical additive ED50 obtained using the PharmToolsPro software.

B. Results

1. Nefopam Alone

The subcutaneous administration of nefopam brings about a dose-dependent inhibition of the number of cramps induced by acetic acid in mice (Table 1). The measured ED50 of nefopam is 2.395±0.215 mg/kg.

2. Ibuprofen Alone

The ibuprofen administered by the subcutaneous route reduces in a dose-dependent manner the number of cramps induced by acetic acid in mice, with an ED50 of 18.581±2.398 mg/kg (Table 1).

This ED50 value is to be compared with the values obtained in the same model with administration by the oral route. In this context, the ibuprofen thus demonstrated a significant antinociceptive activity from 30 mg/kg (Dolezal & Kusiak (2002) *Physiol Res.* 51:179-184) or with an ED50 of 95 mg/kg (Jones et al. (2005) *J. Pharmacol. Exp. Ther.* 312: 726-732).

TABLE 1

Characteristic effects of nefopam and ibuprofen administered alone

| Products (mg/kg) | n | Number of cramps (mean ± sem) | % variation | ANOVA |
|---|---|---|---|---|
| Nefopam | | | | |
| 0 | 18 | 37.1 ± 2.8 | | |
| 0.3 | 9 | 33.6 ± 3.8 | −9 | ns |
| 1.0 | 10 | 28.0 ± 6.3 | −25 | ns |
| 3.0 | 18 | 16.7 ± 2.0 | −55 | $p < 0.05$ |
| 10.0 | 10 | 7.1 ± 1.7 | −81 | $p < 0.05$ |
| 20.0 | 10 | 0.6 ± 0.3 | −98 | $p < 0.05$ |
| ED50 (mg/kg) 2.395 ± 0.215 | | | | |
| Ibuprofen | | | | |
| 0 | 18 | 37.6 ± 1.5 | | |
| 1 | 10 | 40.2 ± 3.2 | +7 | Ns |
| 3 | 10 | 43.0 ± 6.6 | +14 | Ns |
| 10 | 10 | 26.8 ± 3.9 | −29 | Ns |
| 20 | 9 | 22.0 ± 2.0 | −41 | $p < 0.05$ |
| 30 | 9 | 12.1 ± 2.7 | −68 | $p < 0.05$ |
| 50 | 9 | 5.9 ± 1.3 | −84 | $p < 0.05$ |
| 100 | 9 | 6.0 ± 1.4 | −84 | $p < 0.05$ |
| ED50 (mg/kg) 18.581 ± 2.398 | | | | |

($p < 0.05$: ANOVA statistical test followed by Bonferroni or Dunn)

3. Nefopam-Ibuprofen Combination

Firstly, using the PharmToolsPro software, the fixed proportion of each product for a level of efficacy of 50% and the theoretical ED50 which is located on the additivity line are determined in accordance with Tallarida (2000) op. cit. A proportion of 0.114 for nefopam and 0.886 for ibuprofen and a theoretical ED50 of 10.495±1.205 mg/kg are thus obtained.

Secondly, compositions having a proportion of 11.4% of nefopam and 88.6% of ibuprofen are studied in the animal model in order to obtain an experimental ED50 which will be compared with the theoretical ED50 of the additivity line. Table 2 shows the experimental results obtained. The experimental ED50 is 5.870±0.425 mg/kg (corresponding to 0.669±0.048 mg/kg of nefopam and 5.201±0.277 mg/kg of ibuprofen).

Then, finally, the experimental ED50 is placed on the isobologram obtained from the data of Table 1 (FIG. 1). It is observed that the experimental ED50 of the nefopam-ibuprofen combination is located below the additivity line, where the theoretical ED50 corresponding to a simple additivity is located. The interaction between the nefopam and the ibuprofen is therefore in the supra-additivity zone indicating a synergistic relationship between the two compounds. In addition, the statistical analysis gives a $t_{experimental}$ of 4.276 which is greater than the $T_{theoretical}$ of 2.381, and consequently the difference between the experimental ED50 and the theoretical ED50 is significant.

TABLE 2 effect of the co-administration of nefopam and ibuprofen

| Nefopam (mg/kg) | Ibuprofen (mg/kg) | n | Number of cramps (mean sem) | % variation | ANOVA |
|---|---|---|---|---|---|
| 0 | 0 | 9 | 27.9 ± 3.1 | | |
| 0.075 | 0.58 | 10 | 27.7 ± 4.1 | −1 | ns |
| 0.15 | 1.16 | 10 | 22.4 ± 4.2 | −20 | ns |
| 0.30 | 2.32 | 10 | 18.1 ± 3.6 | −35 | ns |
| 0.60 | 4.65 | 8 | 16.6 ± 3.1 | −41 | ns |
| 1.20 | 9.30 | 9 | 9.2 ± 2.3 | −67 | $p < 0.05$ |
| 2.40 | 18.60 | 10 | 7.0 ± 1.5 | −75 | $p < 0.05$ |
| 4.80 | 37.20 | 9 | 1.7 ± 1.0 | −94 | $p < 0.05$ |
| ED50 (mg/kg) 5.870 ± 0.425 | | | | | |

($p < 0.05$: ANOVA statistical test followed by Bonferroni or Dunn)

The invention claimed is:

1. A pharmaceutical composition comprising as active substances a therapeutically effective amount of:
   a) nefopam hydrochloride
   or a pharmaceutically acceptable salt thereof; and
   b) ibuprofen
   or a pharmaceutically acceptable salt thereof;
   wherein the nefopam hydrochloride and ibuprofen, or pharmaceutically acceptable salts thereof, exert a synergistic analgesic effect, and are optionally combined with one or more pharmaceutically acceptable excipients.

2. The pharmaceutical composition of claim 1, comprising a unit dose of from 1 to 120 mg of the nefopam hydrochloride or of a pharmaceutically acceptable salt thereof.

3. The pharmaceutical composition of claim 1, comprising a unit dose of from 1 to 2400 mg of the ibuprofen or of a pharmaceutically acceptable salt thereof.

4. The pharmaceutical composition of claim 1, suitable for administration by the oral, injectable or local route.

5. A method for inducing analgesia or for the treatment of pain in an individual, comprising administering to the individual a therapeutically effective amount of the composition of claim 1
   wherein the nefopam hydrochloride and ibuprofen, or pharmaceutically acceptable salts thereof, exert a synergistic analgesic effect and are optionally combined with one or more pharmaceutically acceptable excipients.

6. The method of claim 5, comprising a unit dose of from 1 to 120 mg of the nefopam hydrochloride or of a pharmaceutically acceptable salt thereof.

7. The method of claim 5, comprising a unit dose of from 1 to 2400 mg of the ibuprofen or of a pharmaceutically acceptable salt thereof.

8. The method of claim 5, wherein the nefopam hydrochloride, or a pharmaceutically acceptable salt thereof, is administered by a route selected from the group consisting of the intravenous route, the oral route, and the intramuscular route.

9. The method of claim 5, wherein the ibuprofen, or a pharmaceutically acceptable salt thereof, is administered by a route selected from the group consisting of the oral route, an injectable route, and a local route.

10. The pharmaceutical composition of claim 1, comprising a) nefopam hydrochloride at a dose of at least 1.20 mg/kg and b) ibuprofen at a dose of at least 9.30 mg/kg.

* * * * *